US00PP32195P2

(12) United States Plant Patent
Bergman

(10) Patent No.: US PP32,195 P2
(45) Date of Patent: Sep. 15, 2020

(54) ***LANTANA* PLANT NAMED 'LANZ0030'**

(50) Latin Name: ***Lantana camara* L.**
Varietal Denomination: LANZ0030

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,590

(22) Filed: May 3, 2019

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./226, 227
See application file for complete search history.

*Primary Examiner* — Susan McCormick Ewoldt
(74) *Attorney, Agent, or Firm* — Dale Skalla

(57) ABSTRACT

A new *Lantana* plant named 'LANZ0023' having dark orange mature flower color, excellent flower production, large plant size and uniform widely spreading plant habit with dark green foliage.

1 Drawing Sheet

Latin name of the genus and species of the plant claimed: *Lantana camara* L.

Varietal denomination: 'LANZ0030'.

BACKGROUND OF THE NEW PLANT

The present invention comprises a new *Lantana*, botanically known as *Lantana camara* L., and hereinafter referred to by the variety name 'LANZ0030'.

'LANZ0030' is a product of a planned breeding program. The new cultivar 'LANZ0030' has dark orange mature flower color, excellent flower production, large plant size and uniform widely spreading plant habit with dark green foliage.

'LANZ0030' originates from an open hybridization in an outdoor field in August, 2014 in Gilroy, Calif. The female parent was identified as 'Balluced' (PPAF), not patented, a commercially available variety having red flower color, smaller flower size and a much smaller plant size. The male parent of 'LANZ0030' is unknown.

The seed was sown in March, 2015 in a greenhouse in Gilroy, Calif., and 'LANZ0030' was selected as one flowering plant within the progeny of the stated cross in June, 2015.

The first act of asexual reproduction of 'LANZ0030' was accomplished when vegetative cuttings were propagated from the initial selection in August 2015 in a greenhouse in Gilroy, Calif.

BRIEF SUMMARY OF INVENTION

Horticultural examination of plants grown from cuttings of the plant initiated in August, 2015, in Gilroy, Calif., and continuing thereafter, has demonstrated that the combination of characteristics as herein disclosed for 'LANZ0030' are firmly fixed and are retained through successive generations of asexual reproduction.

'LANZ0030' has not been observed under all possible environmental conditions. The phenotype may vary significantly with variations in environment such as temperature, light intensity, and day length.

A Plant Breeder's Right for this cultivar has not yet been applied for. 'LANZ0030' has not been made publicly available prior to the effective filing date of this application, notwithstanding any disclosure that may have been made less than one year prior to the effective filing date of this application by the inventor or another who obtained 'LANZ0030' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

Figure 1:
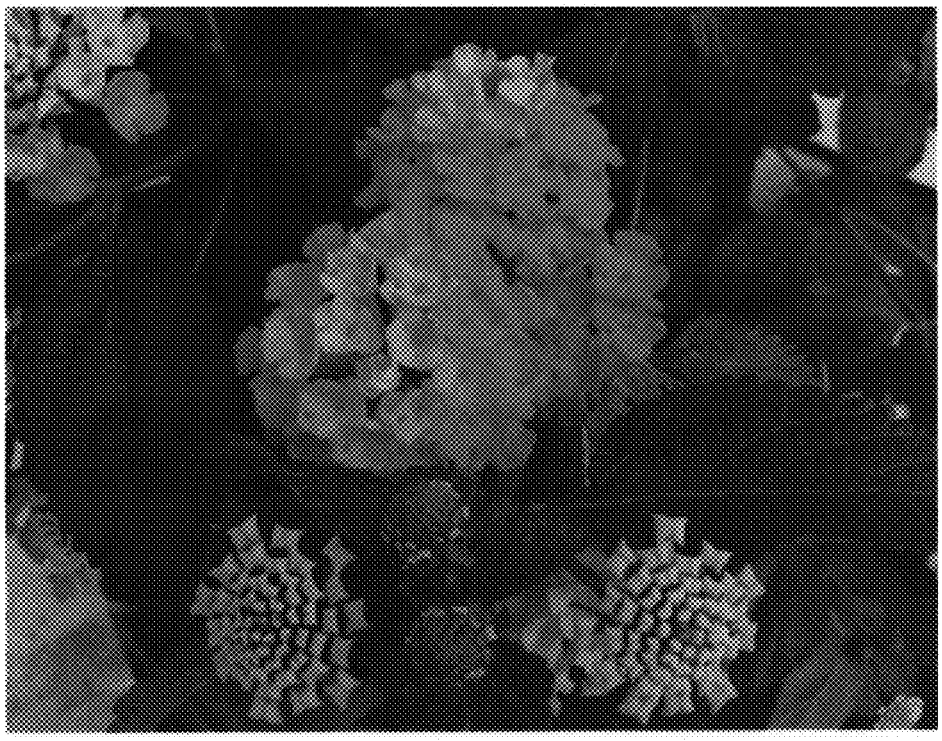
Figure 2:
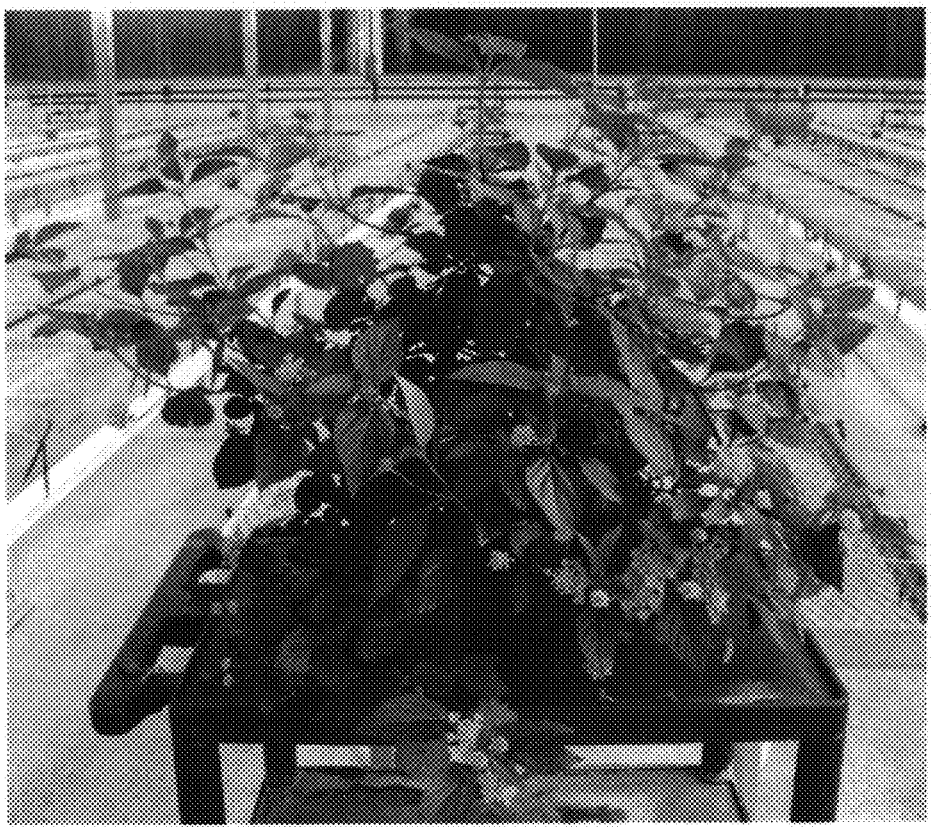

The accompanying photographic drawings show typical flower and foliage characteristics of 'LANZ0030' with colors being as true as possible with an illustration of this type. The photographic drawings show in FIG. 1 a close view of an inflorescence, and in FIG. 2 a whole flowering plant.

DETAILED BOTANICAL DESCRIPTION

The plant descriptions and measurements were taken in Gilroy, Calif. in April 2019. The plants were approximately 8 months old and were growing in gallon pots in a greenhouse.

The aforementioned photographs show those same plants as used for the description were taken in Gilroy, Calif. in April 2019 and show 8 month old plants from an indoor trial.

Color references are made to The Royal Horticultural Society Colour Chart (R.H.S.) 2001.

TABLE 1

DIFFERENCES BETWEEN THE NEW VARIETY 'LANZ0030' AND A MOST SIMILAR VARIETY

| | 'LANZ0030' | 'Balucraim' (Not patented) |
|---|---|---|
| Flower color: | Dark orange | Red |
| Flower size: | Larger | Smaller |
| Seed set: | Moderate | Few |

Plant:

*Form, growth and habit.*—Semi-woody, grown as an annual or perennial; large and dense mounding habit; very well branched.

*Plant height.*—43 cm.

*Plant height (inflorescence included).*—46 cm.

*Plant width.*—79 cm.

Foliage:

*Type.*—Opposite.

*Immature, leaf color, upper surface.*—RHS 136A.

*Lower surface.*—RHS 137B.

*Mature, leaf color, upper surface.*—RHS 139A.

*Lower surface.*—RHS 137B.

*Length.*—8.0-9.0 cm.

*Width.*—4.3-4.9 cm.

*Shape.*—Lanceolate.

*Base shape.*—Attenuate.

*Apex shape.*—Mucronate.

*Margin.*—Dentate.

*Texture, upper surface.*—Hairy.

*Texture, lower surface.*—Hairy.

*Pattern of veining.*—Pinnate.

*Petioles color.*—RHS 137A.

*Petioles length.*—1.5-2.2 cm.

*Diameter of petiole.*—0.20 cm.

*Texture (upper and lower surface).*—Very short hairs.

Stem:

*Color of stem.*—RHS 146C.

*Length of stem.*—34-48 cm.

*Diameter.*—0.25-0.35 cm.

*Length of internodes.*—4.8-12.0 cm.

*Texture.*—Some hairs.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 40-48.

*Quantity of inflorescences per plant.*—About 51.

*Lastingness of individual blooms on the plant.*—About 3 weeks (depending on temperatures).

*Fragrance.*—Slightly spicy.

*Umbel horizontal diameter.*—4.4-4.6 cm.

*Umbel vertical height.*—3.2 cm.

*Peduncle color.*—RHS 146C.

*Length of peduncle.*—6.8-8.7 cm.

*Peduncle diameter.*—0.15 cm.

*Texture.*—Hairs.

Flower:

*Floret form.*—Corolla salver-shaped to shallow cup-shaped, with a relatively long tube at the base; each flower subtended by a single bract.

*Length of floret.*—1.9-2.1 cm.

*Width of floret.*—1.15 cm.

*Depth of floret.*—1.3 cm.

*Young floret, color upper surface.*—RHS 17A.

*Young floret, color lower surface.*—RHS 17C.

*Mid age floret, color upper surface.*—RHS 28A.

*Mid age floret, color lower surface.*—Closest to RHS 25C.

*Mature florets, color upper surface.*—RHS 34A.

*Mature floret, color lower surface.*—RHS 169B and RHS 16B.

*Apex shape.*—Rounded.

*Degree of lobation.*—Moderate.

*Margin.*—Entire.

*Base.*—Fused.

*Texture, upper surface.*—Smooth.

*Lower surface.*—Smooth.

*Tube, color outer surface.*—RHS 22C.

*Tube, color inner surface.*—RHS 22B.

*Tube, length.*—0.9-1.1 cm.

*Tube, diameter (at opening).*—0.2 cm.

*Tube, texture outer surface.*—Very small hairs.

*Inner surface.*—Smooth.

Bud (just before opening):

*Color.*—RHS 15C.

*Length.*—1.1 cm.

*Width.*—0.4 cm at the apex.

*Shape.*—Tubular with a flared apex.

Bract:

*Color.*—Closest to RHS 137A.

*Length.*—0.5-1.3 cm.

*Diameter.*—0.2 cm.

*Texture, upper surface.*—Small hairs.

*Lower surface.*—Small hairs.

Calyx:

*Number of sepals.*—5, fused sepals forming a short tube around the base of the floret.

*Color of sepals.*—RHS 145A.

*Length of sepals.*—0.25 cm.

*Width of sepals.*—0.15 cm.

*Apex shape.*—Obtuse.

*Apex margins.*—Entire.

*Texture, outer surface.*—Small hairs.

*Inner surface.*—Smooth.

Reproductive organs:

*Gynoecium.*—

*Pistil quantity.*—One.

*Length.*—0.5 cm.

*Style color.*—RHS 149D.

*Style length.*—0.3 cm.

*Stigma color.*—RHS 149A.

*Ovary color.*—RHS 142B.

*Ovary length.*—0.1 cm.

*Ovary diameter.*—0.05 cm.

*Androecium.*—

*Stamen quantity.*—4.

*Color of filaments.*—RHS 159D.

*Length filaments.*—0.05 cm.

*Anther color.*—RHS 4C.

*Length of anthers.*—0.1 cm.

*Color of pollen.*—RHS 4D.

*Pollen amount.*—Scant.

*Fertility/seed set.*—Moderate.

*Disease/pest resistance.*—Has not been determined to date.

*Temperature tolerance.*—Very heat tolerant.

*Hardiness zone.*—Hardy to Zone 9B.

What is claimed is:

1. A new and distinct variety of *Lantana* plant named 'LANZ0030' substantially as illustrated and described herein.

* * * * *